(12) United States Patent
LaFleur et al.

(10) Patent No.: US 8,034,305 B2
(45) Date of Patent: Oct. 11, 2011

(54) CONTAINER SEGMENT ASSEMBLY

(75) Inventors: Cedrick James LaFleur, Cypress, TX (US); Edward Alan Johnson, Ft Worth, TX (US)

(73) Assignee: Abbott Laboratories, Abbott Park, IL (US)

( * ) Notice: Subject to any disclaimer, the term of this patent is extended or adjusted under 35 U.S.C. 154(b) by 684 days.

(21) Appl. No.: 11/778,708

(22) Filed: Jul. 17, 2007

(65) Prior Publication Data

US 2009/0020662 A1    Jan. 22, 2009

(51) Int. Cl.
*B01L 3/00* (2006.01)
*F04B 19/00* (2006.01)
*G01N 21/00* (2006.01)
*G01N 31/00* (2006.01)
*G01N 33/00* (2006.01)
*A47B 73/00* (2006.01)

(52) U.S. Cl. .............................. 422/504; 422/64; 211/74

(58) Field of Classification Search .................. 422/102; 248/145
See application file for complete search history.

(56) References Cited

U.S. PATENT DOCUMENTS

| 4,965,049 A | * | 10/1990 | Lillig et al. | 422/68.1 |
| 5,294,404 A | * | 3/1994 | Grandone et al. | 422/64 |
| 5,320,809 A | * | 6/1994 | Dunn et al. | 422/64 |
| 5,324,481 A | * | 6/1994 | Dunn et al. | 422/64 |
| 5,795,784 A | | 8/1998 | Arnquist et al. | |
| 5,856,194 A | | 1/1999 | Arnquist et al. | |
| 6,065,617 A | * | 5/2000 | Cohen et al. | 211/74 |
| 6,074,617 A | * | 6/2000 | DeYoung et al. | 422/104 |
| 6,190,617 B1 | | 2/2001 | Clark et al. | |

* cited by examiner

*Primary Examiner* — In Suk Bullock
*Assistant Examiner* — Bryan Kilpatrick
(74) *Attorney, Agent, or Firm* — Timothy P. Lucier

(57) ABSTRACT

A container segment assembly suitable for use with a carousel of an analytical instrument, including (a) a container rack having the shape of a rectangular parallelepiped, the container rack capable of receiving containers in a substantially linear row and (b) a container segment having a frame. The frame has an arcuate shape, whereby the container segment can be mounted onto a corresponding arcuate portion of the carousel of the analytical instrument. The frame further defines a receptacle capable of receiving the container rack. The major dimension of the receptacle is substantially aligned as a chord of the arcuate-shaped frame of the container segment.

11 Claims, 3 Drawing Sheets

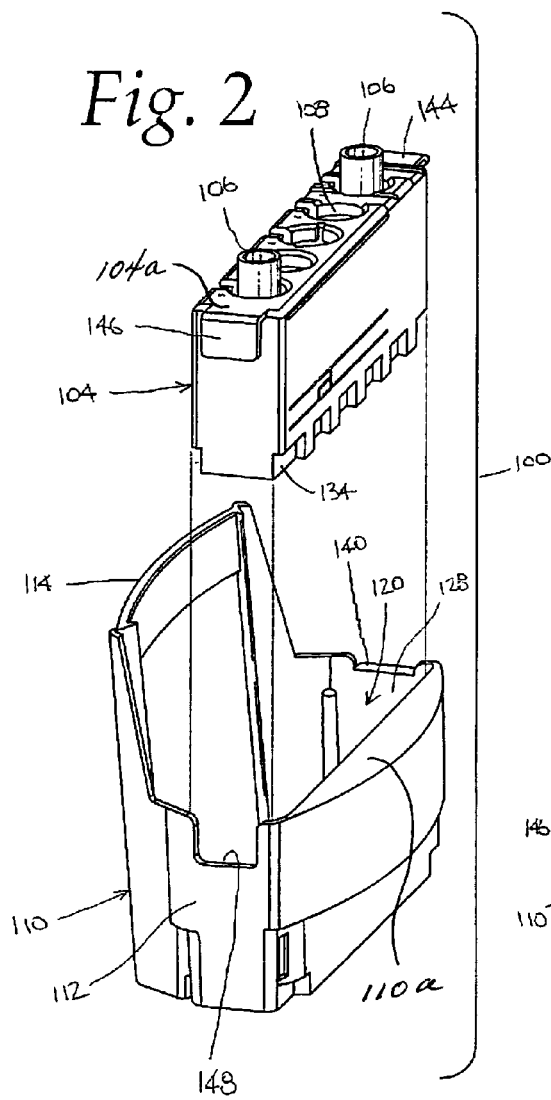
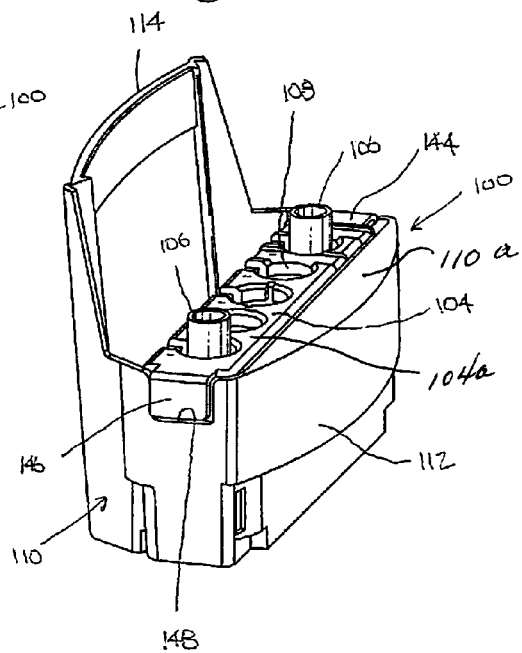

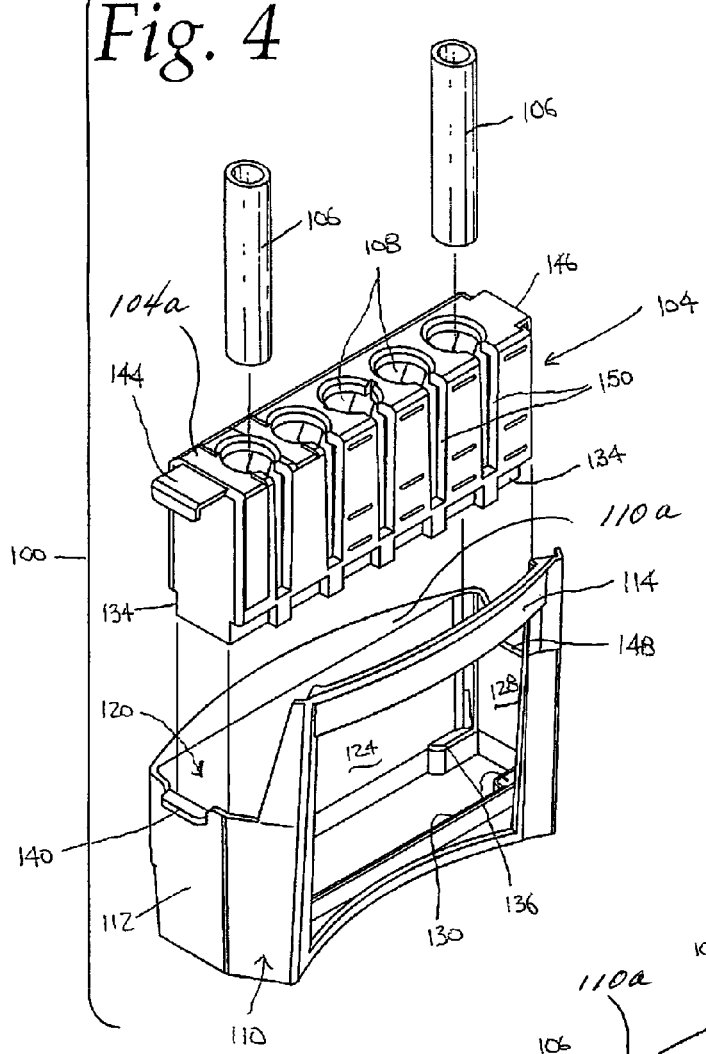
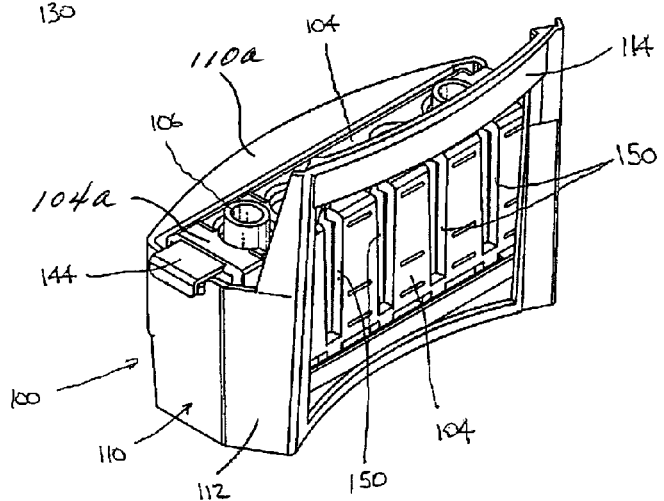

CONTAINER SEGMENT ASSEMBLY

CROSS REFERENCE TO RELATED APPLICATION(S)

Not applicable.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The present invention relates to analytical instruments, and, more particularly, to handling samples to be analyzed by different analytical instruments.

BACKGROUND OF THE INVENTION

Automated analytical instruments are widely used to run a variety of tests on numerous different samples. For example, medical care often requires that blood and other biological samples be tested for a variety of reasons, such as to determine whether or not certain materials are present in the samples. Such instruments may be advantageously used to reduce labor costs and provide reliable, repeatable, test results, with many instruments operating continuously in a random access fashion in order to handle a variety of samples at the same time.

Of course, it will be appreciated that a large number of different tests and testing procedures may be performed to obtain many different types of information. For example, a doctor faced with one set of symptoms may be looking to see one thing to possibly confirm one diagnosis, while another set of symptoms may require looking for a completely different diagnosis. Therefore, it is often not possible, or it is prohibitively expensive, for a laboratory to have a single instrument with the capability to perform all possible tests. Moreover, because various tests may be performed more frequently than others, and because certain tests may consume more time than others, it is often most efficient for a laboratory to have a plurality of different instruments for selected types of tests.

In many instances, however, a single sample or group of samples may require a plurality of tests which may require the use of more than one instrument. In those instances, the samples will typically be manually transferred from one instrument to another instrument. In those instances in which the instruments have different configurations, however, the manual transfer of a plurality of sample containers from one instrument to another instrument can require extensive handling of the containers on account of the need to individually transfer each container from one instrument to another instrument. For example, linear container racks for a plurality of sample containers can easily be transferred from one instrument that uses linear container racks to another instrument that also uses linear container racks by allowing entire racks to be transferred with their associated sample containers. However, when the latter instrument to be used for subsequent testing has arcuate-shaped racks, such as, for example, an instrument having a circular-shaped element for holding sample containers, e.g., a carousel, it has been necessary for operators to manually remove each sample container from the linear container racks and move the sample containers one by one to an arcuate-shaped rack for the circular-shaped element of the other instrument. The same problem arises when running of tests in an instrument having linear container racks follows running of tests in an instrument having arcuate-shaped racks.

Handling of sample containers individually can be expensive not only because of the labor costs involved, but also because of inefficient use of the expensive instruments, which instruments may be forced to sit idle while awaiting the sample containers to be transferred. Further, handling of sample containers always involves a risk of error and/or accidents, and consequently, additional handling of sample containers not only increases that risk but also increases the risk of potential contamination or other damage to the samples, which could lead to erroneous test results. Of course, additional handling of the samples by the operator also increases the risk to the operator when the samples are potentially hazardous.

The present invention is directed toward overcoming one or more of the problems set forth above.

SUMMARY OF THE INVENTION

In one aspect, this invention provides a container segment for use with a circular-shaped element, e.g., a carousel, of an analytical instrument. The container segment includes a frame having an arcuate shape, which frame is constructed for mounting onto a correspondingly arcuate-shaped portion of the circular-shaped element of the analytical instrument. The frame defines a receptacle in the shape of a rectangular parallelepiped, which receptacle is capable of receiving a container rack having the shape of a rectangular parallelepiped, wherein the major dimension of the receptacle is substantially aligned as a chord of the frame having the arcuate shape.

In one embodiment of this aspect of the present invention, the frame further includes a handle.

In another embodiment of this aspect of the present invention, the receptacle is configured to receive the container rack in a single orientation only.

In another aspect, this invention provides a container segment assembly suitable for use with a circular-shaped element, e.g., a carousel, of an analytical instrument. The container segment assembly includes (a) a container rack having the shape of a rectangular parallelepiped, the container rack capable of receiving containers, e.g., sample containers, in a substantially linear row and (b) a container segment having a frame. The frame has an arcuate shape, which frame is constructed for mounting onto a correspondingly arcuate-shaped portion of the circular-shaped element of the analytical instrument. The frame defines a receptacle in the shape of a rectangular parallelepiped, which receptacle is capable of receiving a container rack having the shape of a rectangular parallelepiped, wherein the major dimension of the receptacle is substantially aligned as a chord of the frame having the arcuate shape.

In one embodiment of this aspect of the present invention, the container rack is capable of supporting each container in a substantially vertical orientation. The container rack further includes elongated openings on one elongated side of the container rack to allow reading of labels adhered to the containers. The major dimension of each elongated opening is oriented in the vertical direction.

In another embodiment of this aspect of the present invention, the receptacle of the container segment has four sides, three of which sides are bounded by walls of the frame of the container segment and the fourth of which sides is not bounded by a wall of the frame of the container segment. This fourth side of the receptacle corresponds to an elongated side of the container rack.

In a further embodiment, an ear located on one end of the container rack is receivable by a slot in one end of the container segment. In still a further embodiment, a second ear located on the end of the container rack opposite to that containing the ear mentioned previously cooperates with a lip to releasably hold the container rack in place. The lip is on the end of the container segment opposite to the end where the slot in the container segment is located.

In another embodiment of this aspect of the present invention, the frame includes a handle.

In another aspect, this invention provides a method of analyzing samples on a first analytical instrument that is constructed to receive a container rack in the shape of a rectangular parallelepiped, which container rack is capable of holding a plurality of containers, e.g., sample containers, and a second analytical instrument having a circular-shaped element, e.g., a carousel, that is constructed to receive a container segment comprising a frame having an arcuate shape. The method comprises the steps of:

(a) providing a container rack having the shape of a rectangular parallelepiped, which container rack is constructed to receive a plurality of containers in a substantially linear row;

(b) providing an container segment comprising a frame having an arcuate shape, the container segment constructed to be mounted to a corresponding arcuate portion of a circular-shaped element of an analytical instrument, the container segment including a receptacle adapted to receive the container rack:

(c) inserting a plurality of containers into the container rack the containers containing samples;

(d) mounting the container rack containing the containers onto one of the first analytical instrument or the second analytical instrument;

(e) analyzing the samples in the containers using the one of the first analytical instrument or the second analytical instrument;

(f) mounting the container rack onto the other of the first analytical instrument or the second analytical instrument; and (g) analyzing the samples in the containers using the other of the first analytical instrument or the second analytical instrument.

The container rack is mounted to the second analytical instrument by (a) mounting the container rack in the receptacle of the container segment having the arcuate shape, and (b) mounting the container segment to the circular-shaped element of the second analytical instrument, whereby the linear row of the container rack is substantially aligned as a chord of the circular-shaped element of the second analytical instrument.

BRIEF DESCRIPTION OF THE DRAWINGS

FIG. 2 is an exploded perspective view of the assembly of FIG. 1, illustrating the mounting of a container rack in a container segment.

FIG. 3 is a perspective view of the assembly of FIG. 1.

FIG. 4 is an exploded perspective view of the rear of the assembly of FIG. 3, showing the container rack, the container segment, and containers.

FIG. 5 is a perspective view similar to FIG. 4, illustrating the components assembled.

DETAILED DESCRIPTION OF THE INVENTION

Figure 1:
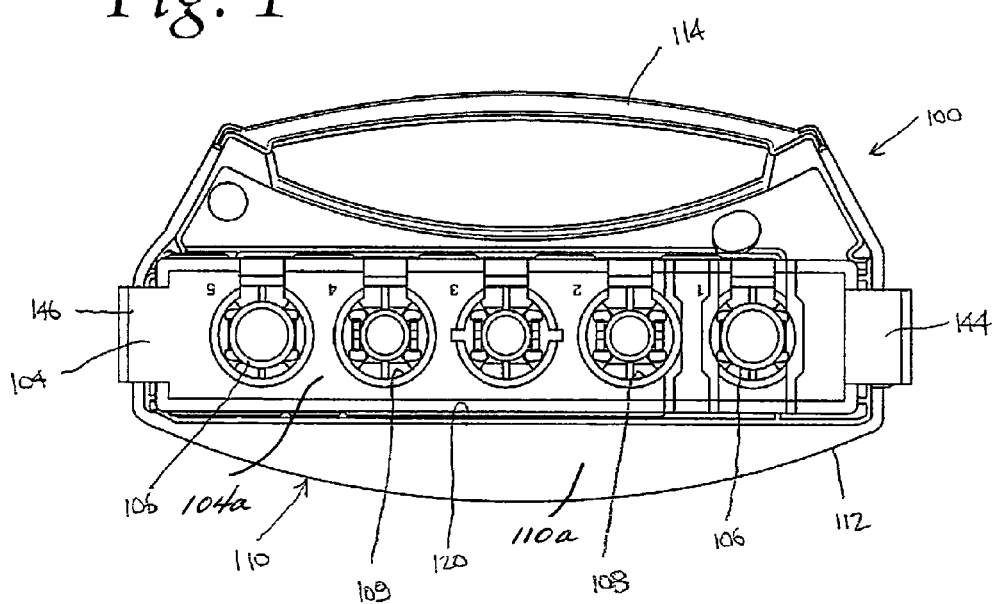
FIG. 1 is a top view of an embodiment of a sample container segment assembly according to the present invention.

As used herein, the expression "circular-shaped element" means a fundamental component of an analytical instrument, which component is shaped like or almost like a circle. The expression circular-shaped element is intended to include elements that comprise 360° of a circle, such as for example a carousel, and elements that comprise portions of a circle, e.g., 90° l of a circle, 180° of a circle, 270° of a circle. As used herein, the term "carousel" means a circular-shaped element comprising a platform capable of supporting a plurality of containers, which platform is further capable of turning about an axis. Representative examples of carousels used in analytical instruments can be found, for example, in U.S. Pat. No. 6,190,617, incorporated herein by reference. As used herein expression "container rack" is intended to include not only a framework or a stand for holding containers that contain samples, but also a framework or a stand for holding containers that contain reagents, diluents, or other items that are processed in an analytical instrument. As used herein, the expressions "arcuate", "arcuate shape", "arcuate-shaped", "arcuate portion", and the like, refer to a three-dimensional item, wherein the length dimension is required to exhibit the shape of a bow, curve, or arch, while neither the width dimension nor the depth dimension is required to exhibit the shape of a bow, curve, or arch. As used herein, the expression "major dimension" means the longer of two dimensions in a plane of an object. As used herein, the term "slot" means a lot narrow groove, opening, notch, or recess.

A container segment assembly 100 according to the present invention is shown in the FIGS. 1-5. The container segment assembly 100 includes a container rack 104 for holding containers 106 (e.g., sample containers, reagent containers, diluent containers) received in suitable receptacles 108 defined by the container rack 104. The containers 106 suitable for use with the container rack 104 described herein include, but are not limited to, Vacutainer®, tubes, test tubes, cuvettes, vials, sample cups, and the like, which containers can be of various sizes and dimensions.

As illustrated in FIGS. 1-5, the container rack 104 has five receptacles 108 aligned in a substantially straight row for carrying up to five containers 106. It should be appreciated that container racks having more or fewer receptacles 108 can be used within the scope of the present invention. The container rack 104 has a shape that is substantially in the form of a rectangular parallelepiped. Such a shape has heretofore been used with automated instruments that handle and move such container racks 104 in linear directions.

As described in greater detail hereinafter, the container segment assembly 100 also includes a container segment 110. The container rack 104 is removably mountable in a container segment 110 in accordance with at least some aspects of the present invention.

The container segment 110 can be received on a carousel of an automated analytical instrument (e.g., in an automated, continuous, and random access analytical system) as is known in the art and as disclosed, for example, in U.S. Pat. No. 6,190,617 B1, the complete disclosure of which is hereby incorporated by reference.

The container segment 110 includes a frame 112 having a handle 114 extending above the frame 112 to facilitate handling by an operator. While the frame 112 of the container segment 110 has an arcuate shape, so as to be capable of being mounted on a curved or circular-shaped element, such as, for example, a carousel, the container segment 110 also includes a receptacle 120, which receptacle 120 is in the shape of a rectangular parallelepiped. The receptacle 120 is constructed to securely receive a container rack 104, which container rack 104 is also in the shape of a rectangular parallelepiped, in an orientation in which the major dimension of the container rack 104 is substantially aligned as a chord in the container segment 110.

The receptacle 120 of the frame 112 is bounded by a substantially planar front wall 124, as well as end walls 128a and 128b, and a rear lip 130. The substantially planar front wall 124, the end walls 128a and 128b, and the rear lip 130 define a volume that is substantially of the shape of a rectangular parallelepiped. The volume so defined has a configuration and has such dimensions that it can securely accommodate the container rack 104, which, as stated previously, is also in the shape of a rectangular parallelepiped. Moreover, mating recesses 134 formed in the base of the container rack 104 and mating seats 136 formed in the base of the sample segment 110 for the mating recesses 134 can be provided to secure the container rack 104 to the receptacle 120 of the container segment 110. The dimensions of such mating recesses 134 and the dimensions of such mating seats 136 can advantageously be varied so as to indicate improper seating of the container rack 104 in the receptacle 120 if the mating recesses 134 are not oriented properly relative to the mating seats 136. In other words, if, for example, four mating recesses and four mating seats are employed, only if the first mating recess conforms to the first mating seat, the second mating recess conforms to the second mating seat, the third mating recess conforms to the third mating seat, and the fourth mating recess conforms to the fourth mating seat will the container rack 104 conform to the receptacle 120 of the container segment 110. If the dimensions of each conforming pair of mating recesses 134 and mating seats 136 are varied in an appropriate manner, the container rack 104 and the receptacle 120 can be fitted together in only a single orientation. Further, a lip 140 can be provided on the frame 112 to cooperate with an ear 144 on the container rack 104 to releasably hold the container rack 104 in place, as well as to provide a clear indication as to whether the rack 104 is properly seated in the receptacle 120 (see, in particular, FIGS. 4 and 5). Still further, an ear 146 provided on the end of the container rack 104, opposite to the end of the container rack 104 on which the ear 144 is located, mates with a slot 148 in the frame 112 to further assure that the container rack 104 is properly mounted in the frame 112 (see, in particular, FIGS. 2 and 3). When the ear 144 properly mates with the lip 140, and when the ear 146 properly mates with the slot 148, and when the mating recesses 134 properly mate with the mating seats 136, the upper surface 104a of the container rack 104 will be in the same plane as the upper surface 110a of the container segment 110.

Elongated slot openings 150 can also be provided on one side of the container rack 104 for each container receptacle 108, with the side of the container rack 104 having the elongated openings 150 being the side facing the rear of the container segment 110 when the container rack 104 is mounted in the container segment 110. In that configuration, the open area above the lip 130 provides an unobstructed optical path through the elongated openings 150, whereby a suitable reader (e.g., a bar code reader) can read a label with a suitable identification (e.g., a bar code) on each container 106 to identify, for the analytical instrument, which sample is at a given location in the analytical instrument.

OPERATION

According to the method of this invention, samples can be analyzed on a first analytical instrument that is constructed to receive a container rack in the shape of a rectangular parallelepiped, which container rack is capable of holding a plurality of containers, e.g., sample containers. The samples can then be analyzed on a second analytical instrument having a circular-shaped element, e.g., a carousel, the second analytical instrument capable of receiving a container segment comprising a frame having an arcuate shape. According to the method, the container rack 104 having the shape of a rectangular parallelepiped is provided. The container rack is constructed to receive a plurality of containers in a substantially linear row. A container segment 110 comprising a frame 112 having an arcuate shape is provided. The container segment 110 is capable of being mounted to a corresponding arcuate portion of a circular-shaped element of an analytical instrument (not shown). The container segment 110 includes a receptacle 120 constructed to receive the container rack 104. A plurality of containers 106 is inserted into the container rack 104. The containers 106 contain samples. The container rack 104 containing the containers 106 is mounted onto one of the first analytical instrument (not shown) or the second analytical instrument (not shown). The samples in the containers are analyzed by using the one of the first analytical instrument or the second analytical instrument. The container rack 104 is mounted onto the other of the first analytical instrument or the second analytical instrument. Then the samples in the containers 106 are analyzed using the other of the first analytical instrument or the second analytical instrument. The container rack 104 is mounted onto the second analytical instrument by (a) mounting the container rack 104 in the receptacle 120 of the container segment 110 having the arcuate shape, and (b) mounting the container segment 110 to the circular-shaped element of the second analytical instrument, whereby the linear row of the container rack 104 is substantially aligned as a chord of the circular-shaped element of the second analytical instrument.

It should thus be appreciated that sample containers 106 can be efficiently loaded into a single container rack 104, which may thereafter be used with many different analytical instruments, including not only instruments that handle linear container racks 104 but also instruments having carousels that require arcuate-shaped container segments 110. The instruments employing carousels can easily be programmed to adjust for the slight difference in location of individual containers 106 on account of their positioning along chords of the circular arc rather than directly on the circular arc of a carousel (so that, e.g., pipettes controlled by the instrument will be positioned in the proper location for aspirating contents of the container, e.g., samples).

Moreover, it should be appreciated that sample containers 106 can be conveniently moved between different types of instruments, thereby allowing not only more efficient handling, and consequently reducing labor and delay caused by such labor, but also reducing the risk of error or accidents, such as contaminating and/or damaging samples in the containers 106.

Still other aspects, objects, and advantages of the present invention can be obtained from a study of the specification, the drawings, and the appended claims. It should be understood, however, that the present invention could be used in alternate forms where less than all of the objects and advantages of the present invention and preferred embodiment as described above would be obtained.

What is claimed is:

1. A container segment suitable for use with a circular-shaped element of an analytical instrument, said container segment comprising a frame having an arcuate shape and adapted to be mounted onto a corresponding arcuate portion of said circular-shaped element of said analytical instrument, said frame defining a receptacle having the shape of a rectangular parallelepiped, said receptacle capable of receiving a container rack having the shape of a rectangular parallelepiped, wherein the major dimension of said receptacle is substantially aligned as a chord of the arcuate-shaped frame.

2. The container segment of claim 1, wherein said frame further comprises a handle.

3. The container segment of claim 1, wherein said receptacle is capable of receiving said container rack in a single orientation only.

4. The container segment of claim 1, wherein said container segment includes a lip for cooperating with an ear of a container rack in order to releasably hold the container rack to the container segment.

5. The container segment of claim 1, wherein said container segment includes a slot to mate with an ear of a container rack to assure that the container rack is properly mounted on the frame of the container segment.

6. A container segment assembly for use with a circular-shaped element of an analytical instrument, said container segment assembly comprising:
    a container rack having the shape of a rectangular parallelepiped, said container rack capable of receiving a plurality of containers in a substantially linear row;
    a container segment having (a) a frame having an arcuate shape, said frame capable of being mounted to a corresponding arcuate portion of the circular-shaped element of said analytical instrument, and (b)
        a receptacle having the shape of a rectangular parallelepiped, said receptacle capable of receiving said container rack, the major dimension of said receptacle being substantially aligned as a chord of the arcuate-shaped frame.

7. The assembly of claim 6, wherein
    said container rack is capable of supporting each container of said plurality of containers in a substantially vertical orientation, said container rack further including elongated opening in a vertical orientation on one side of said container rack to allow reading of labels on said containers; and
    said receptacle having one open side;
    wherein said receptacle is capable of receiving said container rack in an orientation wherein said one side of said container rack corresponds to said one open side of said receptacle.

8. The assembly of claim 7, wherein one end of said container rack includes an ear, said ear being receivable in a slot in one end of said receptacle.

9. The assembly of claim 7, wherein one end of said container rack includes an ear, said ear capable of cooperating with a lip on the frame of the container segment.

10. The assembly of claim 7, said frame further comprising a handle.

11. A method of analyzing samples on a first analytical instrument adapted to receive a container rack having the shape of a rectangular parallelepiped, said container rack capable of holding a plurality of containers and a second analytical instrument having a circular-shaped element adapted to receive an arcuate-shaped frame, said method comprising the steps of:
    providing a container rack having the shape of a rectangular parallelepiped, said container rack adapted to receive containers in a substantially linear row;
    providing a container segment having an arcuate-shaped frame, said arcuate-shaped frame capable of being mounted onto a corresponding arcuate portion of the circular-shaped element of the analytical instrument, said container segment including a receptacle capable of receiving said container rack;
    inserting a plurality of containers into said container rack;
    mounting said container rack onto one of said first analytical or said second analytical instrument;
    analyzing said samples in said containers by means of said one of said first analytical instrument or said second analytical instrument;
    mounting said container rack onto the other of said first analytical instrument or second analytical instrument; and
    analyzing said samples in said containers by means of said other of said first analytical instrument or said second analytical instrument;
    wherein said container rack is mounted to said second analytical instrument by attaching said container rack in said receptacle of said arcuate-shaped frame of said container segment, and attaching said container segment to said circular-shaped element of said second analytical instrument, whereby said linear row of said container rack is substantially aligned as a chord of said arcuate-shaped frame.

* * * * *